(12) United States Patent
Kerr (10) Patent No.: US 9,023,039 B2
(45) Date of Patent: May 5, 2015

(54) ELECTROSURGICAL DEVICE INCLUDING AN OPTICAL SENSOR

(71) Applicant: Covidien LP, Mansfield, MA (US)

(72) Inventor: Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 96 days.

(21) Appl. No.: 13/804,010

(22) Filed: Mar. 14, 2013

(65) Prior Publication Data

US 2014/0025060 A1    Jan. 23, 2014

Related U.S. Application Data

(60) Provisional application No. 61/673,640, filed on Jul. 19, 2012.

(51) Int. Cl.
| | | |
|---|---|---|
| *A61B 18/18* | (2006.01) | |
| *A61B 18/14* | (2006.01) | |
| *A61B 17/00* | (2006.01) | |
| *A61B 18/00* | (2006.01) | |
| *A61B 19/00* | (2006.01) | |

(52) U.S. Cl.
CPC ............... *A61B 18/14* (2013.01); *A61B 18/18* (2013.01); *A61B 18/1402* (2013.01); *A61B 2017/00057* (2013.01); *A61B 2017/00061* (2013.01); *A61B 2018/00642* (2013.01); *A61B 2018/00732* (2013.01); *A61B 2018/00791* (2013.01); *A61B 2018/1412* (2013.01); *A61B 2018/1417* (2013.01); *A61B 2018/1422* (2013.01); *A61B 2019/464* (2013.01)

(58) Field of Classification Search
CPC ..... A61B 18/14; A61B 18/18; A61B 18/1402
USPC .............................................. 606/2–52
See application file for complete search history.

(56) References Cited

U.S. PATENT DOCUMENTS

| 7,156,844 | B2 * | 1/2007 | Reschke et al. ................. 606/41 |
|---|---|---|---|
| 7,393,354 | B2 | 7/2008 | Buchman, II et al. |
| 7,553,686 | B2 | 6/2009 | George et al. |
| 8,298,227 | B2 * | 10/2012 | Leo et al. ........................ 606/41 |
| 8,567,265 | B2 * | 10/2013 | Aeby et al. ............... 73/862.624 |
| 2001/0021843 | A1 * | 9/2001 | Bosselmann et al. ............ 606/2 |
| 2006/0224053 | A1 | 10/2006 | Black et al. |
| 2008/0077200 | A1 | 3/2008 | Bendett et al. |
| 2008/0125775 | A1 | 5/2008 | Morris |
| 2012/0265184 | A1 * | 10/2012 | Sliwa et al. ..................... 606/15 |
| 2012/0296317 | A1 | 11/2012 | Chernov et al. |
| 2012/0296323 | A1 | 11/2012 | Chernov et al. |
| 2012/0296324 | A1 | 11/2012 | Chernov et al. |

\* cited by examiner

*Primary Examiner* — Scott Getzow (57) ABSTRACT

An electrosurgical device and system including a blade operatively coupled to an energy source is disclosed herein. The electrosurgical device includes an optical sensor to monitor physical characteristics of the blade such that the device may automatically regulate the energy supplied to the blade and/or the operator may adjust several parameters including how the blade is removed and how much energy is supplied to the blade. A method of using the device and system is also disclosed.

19 Claims, 5 Drawing Sheets

FIG. 6

ELECTROSURGICAL DEVICE INCLUDING AN OPTICAL SENSOR

CROSS REFERENCE TO RELATED APPLICATION

The present application claims the benefit of and priority to U.S. Provisional Application Ser. No. 61/673,640, filed on Jul. 19, 2012, the entire contents of which are incorporated herein by reference.

BACKGROUND

1. Technical Field

The present disclosure relates generally to an electrosurgical device, and more particularly to an electrosurgical pencil including an electrode and an optical sensor for the detection of changing physical characteristics of the electrode to facilitate desired tissue effects.

2. Background of Related Art

Electrosurgical instruments are commonly used in open and minimally invasive surgical procedures. Because nerve and muscle stimulation cease at 100,000 cycles per second, electrosurgical procedures can be performed safely at radio frequencies ("RF") above 100 kHz. At these frequencies, electrosurgical energy can pass through a patient with minimal neuromuscular stimulation, and without risking electrocution of the patient.

In particular, electrosurgical fulguration comprises the application of electric spark to biological tissue, for example, human flesh or the tissue of internal organs, without significant cutting. The spark is produced by bursts of radio-frequency electrical energy generated from an appropriate electrosurgical generator. Generally, fulguration is used to dehydrate, shrink, necrose or char the tissue. As a result, the instrument is primarily used to stop bleeding and oozing. These operations are generically embraced by the term "coagulation". Meanwhile, electrosurgical cutting includes the use of the applied electric spark to tissue which produces a cutting effect. Electrosurgical sealing includes utilizing both electrosurgical energy and pressure to melt the tissue collagen into a fused mass.

As used herein the term "electrosurgical pencil" is intended to include instruments which have a handpiece which is attached to an active electrode and are used to coagulate, cut and/or seal tissue. The pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically, electrodes of this sort are known in the art as "blade", "loop" or "snare", "needle" or "ball" electrodes.

As mentioned above, the handpiece of the pencil is connected to a suitable electrosurgical source (i.e., a generator), which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

When using electrosurgical instruments in an operation, the active electrode may be rendered less efficient if the tissue distorts or encounters inconsistencies in the tissue. These instances are sensed as a change in the tension required to pass the electrode through the tissue (i.e., "drag").

Also, when using electrosurgical instruments in an operation, the tissue tends to char during the surgical procedure and adhere to the active electrode. When the active electrode is an electrosurgical blade, the charred tissue can in some instances effect the overall performance of the electrosurgical blade. Performance degradation of the blade may reduce the effectiveness of the instrument during the operation. For example, a build up of charred tissue on the active electrode may effect cutting efficiency of the blade. As a result, the surgeon may find it necessary to increase the electrical current to the electrosurgical blade in order to compensate for the degradation of the cutting blade. This raises the possibility that the tissue will be more easily and rapidly charred when contacting the tissue.

Another concern resulting from the build up of charred tissue on the active electrode is that the charred tissue can fracture and contaminate the surgical site which may delay the overall healing process. The build up of charred tissue on the active electrode may also increase drag (i.e., the amount of resistance the body tissue exhibits during cutting). Drag may distort the tissue and consequently alter anatomical relationships which can effect proper suturing, possibly delay healing, and result in more visible scarring.

SUMMARY

The need exists for an electrosurgical pencil which includes drag sensing capabilities to monitor whether the drag force acting on the electrosurgical blade has surpassed a predetermined threshhold level and/or the electrosurgical blade has been displaced or heated beyond a predetermined acceptable level.

The present disclosure relates to devices, systems, and methods for use in an electrosurgical procedure.

In one aspect of the present disclosure, an electrosurgical pencil is disclosed. The electrosurgical pencil may include a housing, e.g. an elongated housing, including a distal portion, which supports an electrode, e.g., a blade, a ball, or a hook, therein. A sensing system is configured and adapted to measure at least one physical characteristic, e.g., temperature and/or strain, of the electrode. The sensing system includes an optical fiber and a light source that transmits light through the optical fiber. An optical sensor is operatively coupled to the optical fiber to detect changes in wavelength of the light emitted from the light source through the optical fiber, wherein a change in the wavelength of the light detected corresponds to a change in the at least one physical characteristic of the electrode.

The optical fiber may include a fiber Bragg grating that reflects particular wavelengths of light corresponding to particular physical characteristics of the electrode, i.e., as the wavelength of light detected changes in response to changing physical characteristics, e.g., strain and/or temperature. The changes in the physical characteristics of the electrode affect whether desired tissue effects are achieved. The fiber Bragg grating may define a periodic pattern and may have a refractive index that changes along the length of the optical fiber. By taking an initial reading of the wavelength, changes from the initial reading may be used to determine changes in the physical characteristics of the electrode.

In another aspect of the present disclosure, an electrosurgical system may include an electrosurgical pencil, such as described above, as well as, a generator that is operatively coupled to the electrosurgical pencil to supply power, e.g., RF energy, to the electrode. The generator is configured and adapted to adjust at least one of its power level and modality, e.g., cutting or coagulation, in response to changes in the at least one physical characteristic, e.g., temperature and/or strain, measured by the sensing system. A control circuit includes a drag circuit, and is used to regulate and/or control RF energy supplied by the generator in response to changes in the physical characteristics detected and/or measured by the sensing system. An increase in one of temperature and strain results in a decrease in the power level supplied by the generator. Conversely, a decrease in one of temperature and strain results in an increase in the power level supplied by the generator. In an embodiment, the control circuit increases power supplied to the electrode when displacement of the electrode results in strain greater than a preset value and decreases power supplied to the electrode when the displacement of the electrode is less than a preset value. The control circuit may prevent power from being delivered to the electrode that exceeds a preset threshold value.

In a further aspect of the present disclosure, a method for performing a surgical procedure includes: (a) initializing an electrosurgical system including a generator, an electrode, and an optical sensor operatively coupled to the electrode; (b) supplying energy to the electrode through the generator; (c) reading a signal produced by the optical sensor in response to a wavelength of light detected by the optical sensor, the signal having a value; (d) decreasing the energy supplied if the value is below a preset value; (e) increasing the energy supplied if the value is greater than a preset value; and (f) resetting the preset value. The generator may automatically provide an appropriate power level and adjust the modality, e.g., cutting or coagulation effects, of the electrode in response to detected changes in the physical characteristics, e.g., strain and/or temperature, of the electrode.

These and other embodiments of the present disclosure will be described in greater detail hereinbelow.

BRIEF DESCRIPTION OF THE DRAWINGS

Embodiments of the present disclosure are described herein with reference to the accompanying drawings, wherein.

DETAILED DESCRIPTION

The present disclosure relates to electrosurgical devices, systems, and methods for using the same in which one or more of the physical characteristics of an electrosurgical blade are monitored to facilitate desired effects upon target tissue. Electrosurgical pencils including sensing capabilities have been previously disclosed. An example of an electrosurgical pencil is described in U.S. Pat. No. 7,393,354, the contents of which are hereby incorporated by reference in its entirety herein.

An electrosurgical pencil 100 is described with reference to FIGS. 1 and 2 and includes an elongated housing 112 configured to support a blade receptacle 114 at a distal end thereof. The blade receptacle 114 is configured to receive and support an electrode 116 within the blade receptacle 114. In some embodiments, the electrode 116 may be shaped as a blade, a ball, a hook, and the like. A distal portion 117 of the electrode 116 extends distally from receptacle 114, and a proximal portion 115 of electrode 116 is retained within the distal end of the housing 112. The electrode 116 may be fabricated from any conductive material, e.g., stainless steel or coated with an electrically conductive material.

The electrosurgical pencil 100 is coupled to an electrosurgical generator 118 via one or more connecting wires 120. The connecting wire(s) 120 includes a current wire 122, which electrically connects the electrosurgical generator 118 and the electrode 116. A casing 121 electrically insulates and encapsulates the current wire 122 to protect the operator from stray electrical currents. By way of example only, the electrosurgical generator 118 may include, any of the following or equivalent generators sold by Covidien of Boulder, Co., FORCE FX™, FORCE 2 ™, FORCE 4™. The electrosurgical generator 118 may be preset to selectively provide an appropriate RF signal, e.g., 1 to 300 watts, for tissue cutting and an appropriate RF signal, e.g., 1 to 120 watts, for tissue coagulation. However, the resultant tissue effects depend upon several variables including the temperature of the blade and the strain exerted upon the blade. Described in greater detail hereinbelow is an optical sensor that monitors such physical characteristics of the blade to facilitate achievement of desired tissue effects.

The generator 118 is configured to operate in a variety of modes. In one embodiment, the generator 118 may operate in the following modes: cut, blend, division with hemostasis, fulgurate and spray. Each of the modes operates based on a pre-programmed power curve that dictates how much power is outputted by the generator 118 at varying impedance ranges of the load (e.g., tissue). Each of the power curves includes a constant power, constant voltage and constant current ranges that are defined by the user-selected power setting and the measured impedance of the load.

In a cut mode, the generator 118 supplies a continuous sine wave at a predetermined frequency (e.g., 472 kHz) having a crest factor of 1.5 or less in the impedance range of 1000 Ω to 2,000Ω. The cut mode power curve may include three regions: constant current into low impedance, constant power into medium impedance and constant voltage into high impedance. In the blend mode, the generator supplies bursts of a sine wave at the predetermined frequency, with the bursts reoccurring at a first predetermined rate (e.g., about 26.21 kHz). In one embodiment, the duty cycle of the bursts may be about 50%. The crest factor of one period of the sine wave may be less than 1.5. The crest factor of the burst may be about 2.7.

The division with hemostasis mode includes bursts of sine waves at a predetermined frequency (e.g., 472 kHz) reoccurring at a second predetermined rate (e.g., about 28.3 kHz). The duty cycle of the bursts may be 25%. The crest factor of one burst may be 4.3 across an impedance range of 100Ω to 2,000Ω. The fulgurate mode includes bursts of sine waves at a predetermined frequency (e.g., 472 kHz) reoccurring at a third predetermined rate (e.g., about 30.66 kHz). The duty cycle of the bursts may be 6.5% and the crest factor of one burst is 5.55 across an impedance range of 100Ω to 2,000Ω. The spray mode will be bursts of sine waves at a predetermined frequency (e.g., 472 kHz) reoccurring at a fourth predetermined rate (e.g., about 21.7 kHz). The duty cycle of the bursts may be 4.6% and the crest factor of one burst may be 6.6 across the impedance range of 100Ω to 2,0000Ω.

The electrosurgical pencil 100 includes an activation button 124 supported on an outer surface of housing 112. The activation button 124 is operable to control a depressible switch 126, which is used to control the electrical energy supplied to the electrode 116. The electrical energy supplied is at a radio frequency ("RF") from about 3 kHz to about 300 GHz or at any other frequency that minimizes risk of neuromuscular damage or electrocution of the patient. A generator 118 is operatively coupled to the electrode 116 to supply RF energy. Various control means, e.g., hand and/or foot actuation and/or automated, may be employed to regulate RF electrical energy supplied by generator 118 to the electrode 116. In an embodiment, a foot switch (not shown) may be electrically coupled to the electrosurgical pencil 100 to control the RF energy supplied to the electrode 116. In an embodiment, the control circuit may include an on/off connection components, as well as high/low power components utilizing a conventional resistive matrix. The control circuit 110 regulates and/or monitors the electrical energy passing through a current wire 122 between depressible switch 126 and receptacle 114.

The electrosurgical pencil 100 further includes a sensor assembly 301 that includes an optical sensor 300, which is operatively coupled to the electrode 116. The optical sensor 300 may be partially or fully embedded within the electrode 116 or may be mounted on the outside of the electrode 116 at any point along the electrode 116, e.g., at the proximal end 115 or the distal end 117 of the electrode 116. The optical sensor 300 may be used for direct sensing of the physical characteristics experienced by the electrode 116, e.g. strain and/or temperature. Although shown and described in connection with direct sensing, in other embodiments, the optical sensor 300 may be used as a transduction element, converting the output of another sensor (not shown), where the change in the physical characteristic being measured is then transduced by the optical sensor 300.

The optical sensor 300 senses and monitors changes in the physical characteristics of the electrode 116. Such physical characteristics include, but are not limited to, strain and temperature, which may affect the effects of the electrode 116 upon the tissue T (FIG. 2A). The optical sensor 300 may also sense and monitor environmental changes at or near the electrode 116. The optical sensor 300 may be used to monitor or measure mechanical displacement/deflection of the electrode 116, i.e., bending of the electrode 116, which may indicate resistance of the tissue T. The optical sensor 300 is described in greater detail below with reference to FIG. 2A.

Figure 2A:
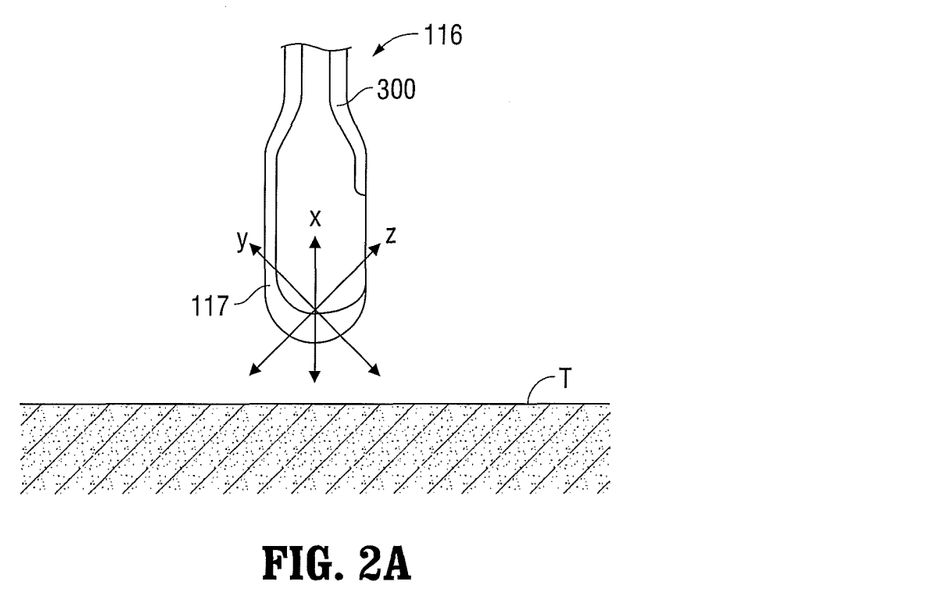
FIG. 2A is an perspective view of the area indicated in FIG. 1 shown relative to tissue.

As shown in FIG. 2A, distal end 117 of the electrode 116 may be moved relative to tissue T along directional arrows x, y, z. The effects upon the tissue T is dependent upon several factors including the shape of the portion of the electrode 116 coming into contact with the tissue T and the movement of the electrode 116 with respect to the tissue T. In an embodiment, where the distal end 117 of the electrode 116 is shaped as shown in FIG. 2A, movement of the electrode 116 along directional arrows x, y will result more in cutting of the tissue T, whereas movement of the electrode 116 along directional arrow z will result in more coagulation of the tissue T.

Figure 2B:
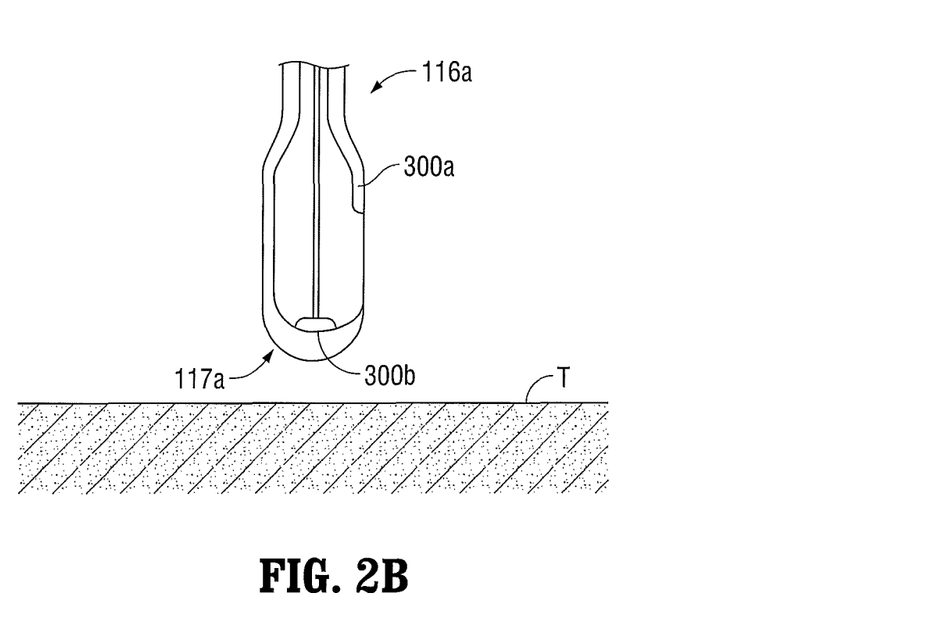
FIG. 2B is a perspective view of the distal end of an electrosurgical pencil including an electrode in accordance with the present disclosure.

In some embodiments, as shown in FIG. 2B, an electrode 116a, which is substantially similar to the electrode 116, includes a first optical sensor 300a, as well as a second optical sensor 300b. The use of more than one optical sensor may facilitate monitoring of more than one physical characteristics, e.g., temperature and strain. For example, the optical sensor 300a may be securely mounted within the electrode 116a, e.g., glued thereto along the entire or substantially the entire length thereof, to provide for strain measurements imposed on the electrode 116a. By providing more than one optical sensor, the individual effects of both temperature and strain upon the optical sensor 300a may be isolated and determined in the following manner. The second optical sensor 300b is mounted to the electrode 116a such that strain does not transfer to the second optical sensor 300B (e.g., only at distal end 117A of the electrode 116A). The second optical sensor 300b may be operatively coupled to a light source (e.g., light source 149) via an optical fiber that is unaffected by the changing physical characteristics. The second optical sensor 300b is only affected by temperature because its placement at the distal end 117a means that strain applied to the electrode 116a is not translated to the second optical sensor 300b. Thus, the optical sensor 300 provides sensor feedback regarding temperature and strain, while the optical sensor 300b provides sensor feedback only regarding temperature. This allows for the determination of the individual effects of both temperature and strain by providing two optical sensors in which one is affected by two variables and another is affected by only one variable.

During an electrosurgical procedure, the characteristics of the tissue T may change such that the tissue T may resist movement of the electrode 116 differently. For example, charred tissue will be relatively tougher and have a tendency to resist cutting. By measuring the three-dimensional strain in the x, y, z coordinates, i.e., the ratio of the deformation of particular points within the electrode 116 relative to the original positioning of those points within the electrode 116, will provide a mechanism to monitor and regulate the effects of the electrode 116 upon the tissue T.

As the drag acting against the distal end 117 of the electrode 116 is increased by increased pressure applied by the operator to overcome the build up of charred tissue on the electrode 116, the deflection and/or displacement of the proximal end 115 of the electrode 116 also increases. The displacement of the proximal end 115 of the electrode 116 is measured by the optical sensor 300. Changes in temperature or strain that are processed by the drag evaluation circuitry 142 (FIG. 1) may be monitored by the operator on a viewing device (not shown), e.g., a monitor or a meter, and/or result in an automatic response by the generator 118 to regulate the supply of RF energy to the electrode 116 to facilitate desired tissue effects, as described in further detail below with respect to FIGS. 4-6.

As the operator uses pencil 100 to cut or coagulate, a user may monitor any significant changes that surpass a predetermined threshold level. These changes alert the operator that either: (1) the advancement of electrode 116 through the tissue site is too fast which may result in the tissue becoming distorted; or (2) that the build up of charred tissue on electrode 116 is approaching a level at which continued advancement of electrosurgical pencil 100 may cause the tissue to become distorted.

Figure 1:
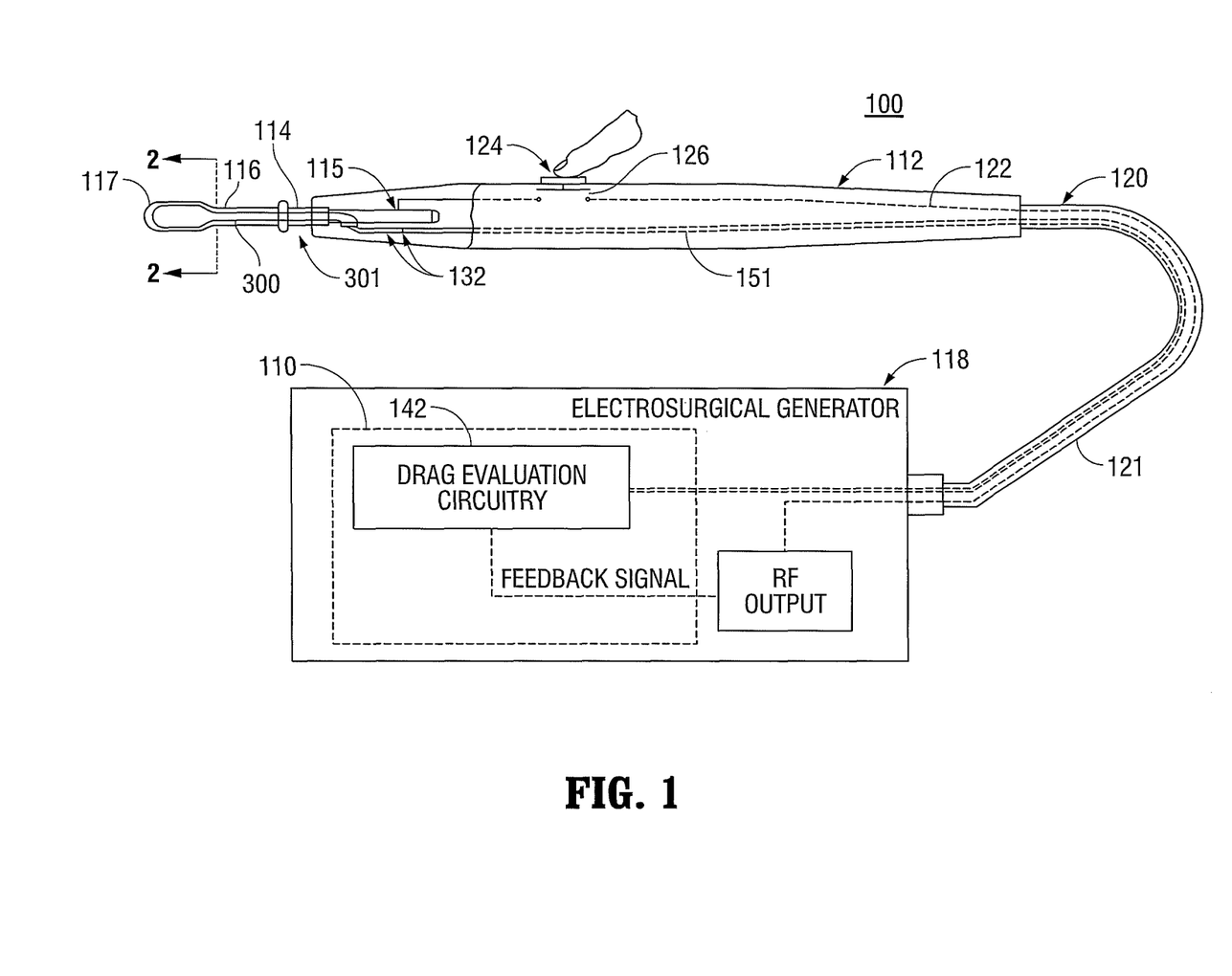
FIG. 1 is a partially broken away side elevational view of an embodiment of an embodiment of an electrosurgical pencil in accordance with the present disclosure.
Figure 4:
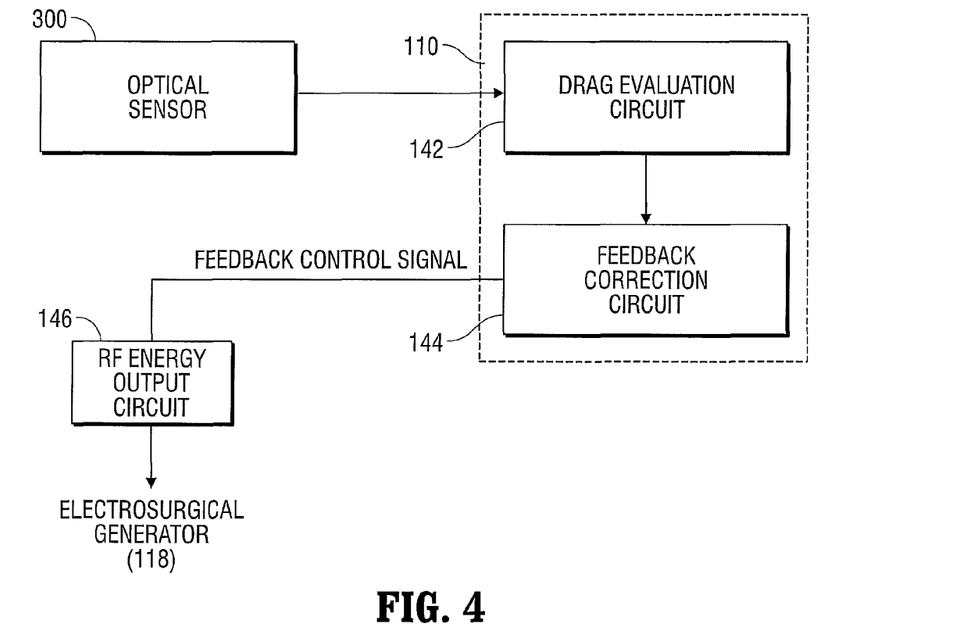
FIG. 4 is a schematic flow chart of the electrosurgical system in accordance with the present disclosure.

As shown in FIGS. 1 and 4, the electrosurgical pencil 100 may be provided with a feedback system, described in greater detail below, connected to the electrosurgical generator. The feedback of the sensed drag is provided as an input to a control circuit 110 in the generator 118 that modulates the generator output waveform. In some embodiments, increased drag would indicate the need for increasing the output current to the active electrode.

Figure 3:
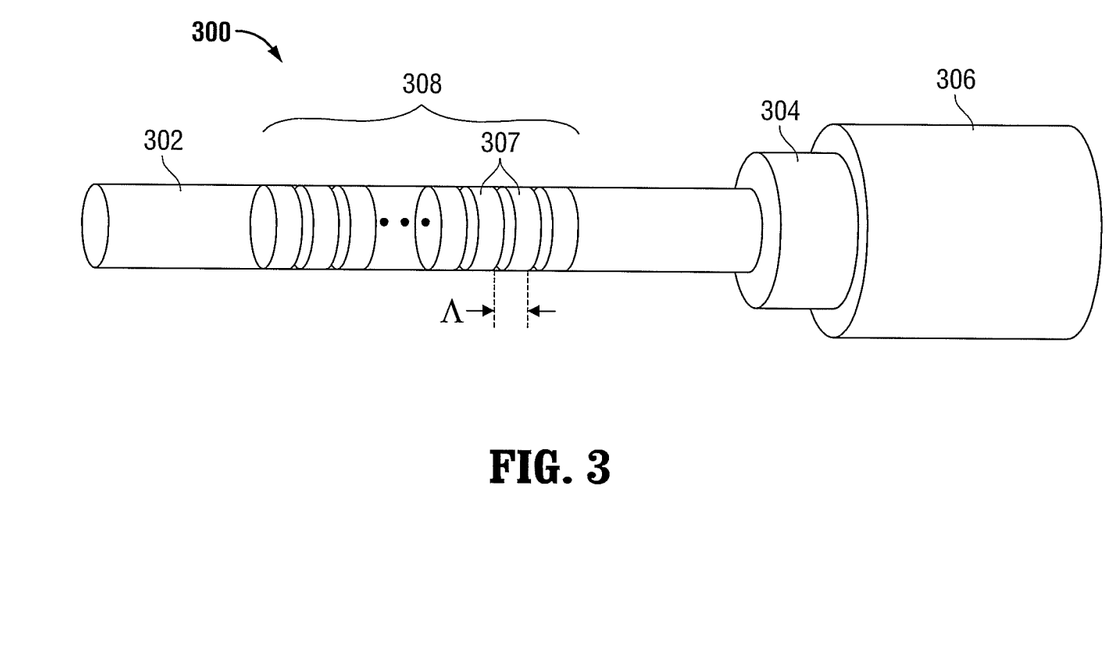
FIG. 3 is a perspective view of an optical fiber including a grating in accordance with the present disclosure.

With reference to FIG. 3, an optical sensor 300 is operatively coupled to the electrode 116 to modulate one or more properties of a propagating light wave, including intensity, phase, polarization, and frequency, in response to parameters, e.g., temperature and strain, being measured. The optical sensor 300 includes a core 302, a cladding 304 disposed around the core 302, and a buffer coating 306 disposed around the cladding 304. The core 302 is an optical fiber, i.e., a thin strand of glass that transmits light within its core. The cladding 304 reflects stray light back into the core 302, minimizing the loss of light through the core 302. The buffer coating 306 provides protection from external conditions and physical damage.

The optical sensor 300 includes a fiber Bragg grating (FBG) 308, which includes a plurality of segments 307 each having a refractive index "n" and spaced a distance "Λ" from one another, i.e., grating period. Reflections from each segment 307 of alternating refractive indices interfere constructively only for a specific wavelength of light called the Bragg wavelength, $\lambda_b$, which is a function of the spacing between the segments 307 and the effective refractive index n. The relationship between the Bragg wavelength $\lambda_b$, the effective refractive index n, and the grating period Λ is provided by the following equation: $\lambda_b = 2*n*\Lambda$. Changes in strain and temperature affect both the effective refractive index n and the grating period Λ of the FBG 308.

The relationship between temperature, strain, and wavelength is provided by the following equation:

$$\frac{\Delta\lambda}{\lambda_0} = k*\varepsilon + \alpha_\delta * \Delta T, \quad (I)$$

where Δλ is the wavelength shift, $\lambda_0$ is the base wavelength, k is a gage factor, which is a difference between 1 and a photo-elastic coefficient, ρ, ε is strain, ΔT is a temperature change, and $\alpha_\delta$ is a change of the refraction index. Since the relationship between the variables is known, monitoring changes in the wavelength provides an effective sensing of mechanical affects from the physical properties of the electrode 116, e.g., temperature and/or strain experienced by the electrode 116.

As the drag against the distal end 117 of the electrode 116 increases, e.g., due to the pressure applied by the operator and/or the build up of charred tissue on the electrode 116, the deflection and/or displacement of the proximal end 115 of the electrode 116 also increases. The displacement of the proximal end 115 of the electrode 116 is measured by the optical sensor 300, which can be monitored by the operator. In an embodiment, a light source 149 (FIG. 5), e.g., a laser, sends light in a particular wavelength through the core 302. When the electrode 116 is at rest, e.g., prior to use or bending of the electrode 116, measurements of the effective wavelength of light through the core 302 may be taken to provide a baseline such that differences from this baseline wavelength may be monitored.

As shown in the schematic of FIG. 4, a feedback mechanism is depicted. Signals from the optical sensor 300 are sent to control circuit 110, which is configured for automated control of an electrosurgical generator 118. The control circuit 110 electrically couples the current wire 122 and activation button 124. The optical sensor 300 converts a small mechanical displacement of blade 116 to an electrical signal which is transmitted through signal wires 132 to a drag evaluation circuit 142 of control circuit 110. The drag evaluation circuit 142 is configured to receive the electrical signal from optical sensor 300 and evaluate or compare the electrical signal against a preset or known value. Drag evaluation circuit 142 then transmits an evaluation signal to a feedback correction circuit 144 of control circuit 110 which, in turn, transmits a feedback control signal to an RF energy output circuit 146 of electrosurgical generator 118. RF energy output circuit 146 instructs electrosurgical generator 118 of the change in power, current or voltage to be supplied to blade 116.

Figure 5:
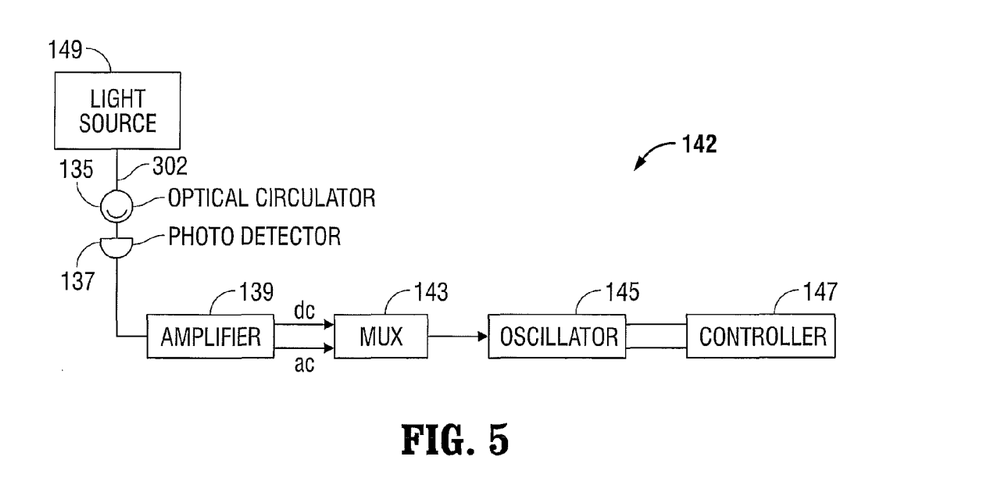
FIG. 5 is a schematic flow chart of a drag circuit in accordance with the present disclosure.

As shown in FIG. 5, light from a light source 149 is continually sent through optical sensor 300 and through the Bragg grating 308 (FIG. 3). A portion of the light, e.g., optical signal, is reflected from the Bragg grating 308, and is reflected back through an optical circulator 135 to a photodetector 137, and is converted into an electrical signal. As the parameters, e.g., strain and/or temperature, change, the light reflected from the Bragg grating 308 correspondingly changes, thereby changing the electrical signal. An amplifier 139 may amplify the electrical signal. The electrical signal may also be filtered through a multiplexer 143 such that a number of optical signals can be carried on a single optical fiber, which is then sampled with an oscilloscope. The sampled signal is processed in a controller 147, which can monitor and record changes in the characteristics of the reflected light, which as discussed correspond to changes in the physical characteristics, e.g., strain and/or temperature, of the electrode 116. In some embodiments, either by using multiple optical sensors 300 or through the use of a multiplexer, e.g, multiplexer 143, multiple characteristics can be monitored, e.g., strain and temperature. The controller 147 may communicate with the generator 118 to regulate the electrical power sent to the electrode 116 automatically, thereby providing desired power output through the electrode 116 for desired tissue effects.

The controller 147 may be any suitable computing device, processing unit, computational circuit, or any type of processor or processing circuit capable of executing a series of instructions that are stored in a memory. The controller 147 may include multiple processors and/or multicore CPUs and may include any type of processor, such as a microprocessor, digital signal processor, microcontroller, or the like.

Figure 6:
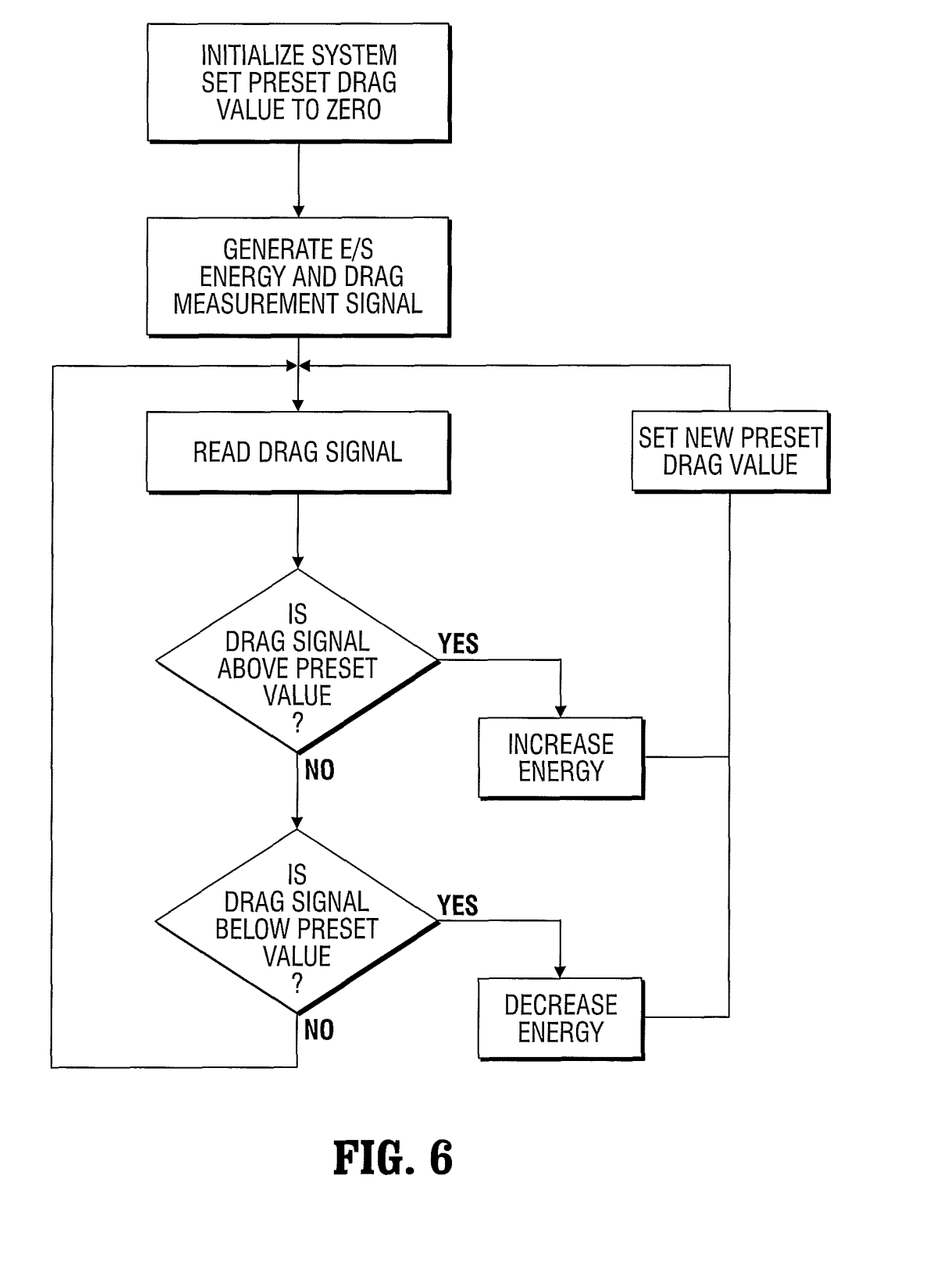
FIG. 6 is a schematic flow chart of a method for controlling an electrosurgical generator output in accordance with the present disclosure.

Operation of the control circuit 110 is described in detail with reference to FIGS. 4-6. Electrosurgical pencil 100 and electrosurgical generator 118 are initialized such that optical sensor 300 of blade 116 is calibrated to produce an initial drag value of zero. The surgeon then sets electrosurgical pencil to a desired "drag value" and activates electrosurgical pencil 100 by depressing activation switch 124, thus permitting energy (i.e., electrical current, voltage, etc.) to flow to blade 116. The user then commences the electrosurgical procedure by touching blade 116 to the target surgical site (e.g., body tissue, skin, organ, etc.) at which time blade 116 begins to displace due to the drag sensed thereon. The displacement due to the drag, in turn, causes optical sensor 300 to produce a drag signal, which is transmitted to control circuit 110 of electrosurgical generator 118. Drag evaluation circuit 142 of control circuit 110 receives the measured drag signal and evaluates or compares the measured drag signal against the preset "drag value."

With reference to FIG. 4, if the measured drag signal is above the preset "drag value", drag evaluation circuit 142 transmits a signal to feedback correction circuit 144 which, in turn, instructs electrosurgical generator 118 to increase the energy output to blade 116. In addition, feedback correction circuit 144 resets the "drag value" to the value of the higher measured drag signal. If the measured drag signal is not above the preset "drag value", drag evaluation circuit 142 evaluates to see if the measured drag signal is below the preset "drag value." If the measured drag signal is below the preset "drag value", drag evaluation circuit 142 transmits a signal to feedback correction circuit 144 which, in turn, instructs electrosurgical generator 118 to decrease the energy output to blade 116. In addition, feedback correction circuit 144 resets the "drag value" to the value of the lower measured drag signal. If the measured drag signal is not below the preset "drag value" the evaluation process repeats from the beginning.

This evaluation process is continually ongoing so long as electrosurgical pencil 100 is activated. In some embodiments, the evaluation process occurs on the order of 100 times per second. In this manner, the power delivered to blade 116 is constantly monitored and adjusted in order to ensure that minimal trauma to the target site occurs. The evaluation rate may be adjusted as needed. For example, a higher rate of evaluation may be desired for more delicate target surgical sites while a reduced rate of evaluation may be desired for hardier target sites. Control circuit 110 may be provided with a cut-off control circuit (not shown). Cut-off control circuit would prevent the power being delivered to blade 116 from exceeding a threshold value in order to prevent electrosurgical pencil 100 from transmitting a damaging amount of energy to the target surgical site.

It should be understood that although the optical sensor including a fiber Bragg grating is shown and discussed as being used as a direct sensing element for strain and temperature, it is within the scope of this disclosure to use fiber Bragg gratins as transduction elements, converting the output of another sensor, which generates a strain or temperature change from the measure and, for example fiber Bragg grating gas sensors use an absorbent coating, which in the presence of a gas expands generating a strain, which is measurable by the grating. Technically, the absorbent material is the sensing element, converting the amount of gas to a strain. The Bragg grating then transduces the strain to the change in wavelength.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Although the foregoing disclosure has been described in some detail by way of illustration and example, for purposes of clarity or understanding, it will be obvious that certain changes and modifications may be practiced within the scope of the appended claims. For example, although shown and described with reference to electrosurgical pencils, the optical sensor described herein may be applied to other surgical instruments to sense and/or monitor changes in the end effector of a surgical instrument to regulate and facilitate desired effects of the end effector upon tissue.

What is claimed is:

1. An electrosurgical pencil, comprising:
   a housing including a distal portion;
   an electrode supported within the distal portion of the housing; and
   an optical sensor assembly configured to measure a temperature of the electrode, the optical sensor assembly including:
   a light source configured to provide light;
   an optical fiber operatively coupled to the light source; and
   an optical sensor operatively coupled to the optical fiber and configured to detect at least one change in a wavelength of the light transmitted from the light source through the optical sensor, wherein the at least one change in the wavelength of the light corresponds to a change in the temperature of the electrode.

2. The electrosurgical pencil of claim 1, wherein the housing is an elongated pencil-shaped housing.

3. The electrosurgical pencil of claim 1, wherein the optical sensor assembly is further configured to measure a strain on the electrode.

4. The electrosurgical pencil of claim 1, wherein the optical sensor includes a fiber Bragg grating that reflects a wavelength of light corresponding to the temperature.

5. The electrosurgical pencil of claim 4, wherein changes in the temperature causes a change in the wavelength.

6. The electrosurgical pencil of claim 4, wherein the fiber Bragg grating includes a plurality of segments disposed in a periodic pattern having a predetermined refractive index.

7. The electrosurgical pencil of claim 1, wherein the optical fiber defines a length and has a refractive index that varies along the length of the optical fiber.

8. The electrosurgical pencil of claim 1, wherein the electrode is selected from the group consisting of a blade, a ball, and a hook.

9. An electrosurgical system, comprising:
   an electrosurgical pencil comprising:
   a housing including a distal portion;
   an electrode supported within the distal portion of the housing; and
   an optical sensor assembly configured to measure a temperature of the electrode, the optical sensor assembly comprising:
   a light source configured to provide light;
   an optical fiber operatively coupled to the light source; and
   an optical sensor operatively coupled to the optical fiber and configured to detect at least one change in a wavelength of the light transmitted from the light source through the optical sensor wherein the at least one change in the wavelength of the light corresponds to a change in the temperature of the electrode; and
   a generator operatively coupled to the electrosurgical pencil to supply at least one radio frequency waveform to the electrode, the generator configured to adjust the at least one radio frequency waveform in response to the change in the temperature of the electrode.

10. The electrosurgical system of claim 9, wherein the generator is configured to operate according to a modality selected from the group consisting of cutting, coagulation, blend, division with hemostasis, fulgration, spray, or combinations thereof.

11. The electrosurgical system of claim 9, wherein the optical sensor assembly is further configured to measure a strain on the electrode and the generator is configured to decrease a power level of the at least one radio frequency waveform in response to an increase in at least one of the temperature or the strain of the electrode.

12. The electrosurgical system of claim 11, wherein the generator comprises a drag circuit configured to adjust the at least one radio frequency waveform in response to the change in at least one of the temperature or strain.

13. The electrosurgical system of claim 12, wherein the drag circuit is configured to decrease power level of the at least one radio frequency waveform in response to the strain on the electrode being greater than a first preset value.

14. The electrosurgical system of claim 13, wherein the drag circuit is configured increase power level of the at least one radio frequency waveform in response to the strain on the electrode being less than a second preset value.

15. The electrosurgical system of claim 14, wherein the drag circuit is configured terminate supply of energy in response to the strain on the electrode being greater than a third preset value.

16. The electrosurgical system of claim 12, wherein the drag circuit is configured to adjust a property of the at least one radio frequency waveform selected from the group consisting of duty cycle and amplitude in response to changes in at least one of the temperature or the strain.

17. A method for performing a surgical procedure, comprising:
 supplying energy to an electrode coupled to a generator, the electrode including an optical sensor;
 transmitting light through the optical sensor from a light source;
 measuring a temperature of the electrode using the optical sensor;
 detecting at least one change in a wavelength of the light transmitted from the light source through the optical sensor wherein the at least one change in the wavelength of the light corresponds to a change in the temperature of the electrode;
 decreasing the energy supplied to the electrode in response to the change in the temperature of the electrode being below a preset value; and
 increasing the energy supplied to the electrode in response to the change in the temperature of the electrode being greater than the preset value.

18. The method of claim 17, further comprising sensing the strain on the electrode.

19. The method of claim 17, further comprising:
 selecting a modality in response to the change in the temperature of the electrode, the modality selected from the group consisting of cutting, coagulation, blend, division with hemostasis, fulgration, spray, or combinations thereof.

* * * * *